United States Patent [19]
Addis

[11] Patent Number: 6,146,357
[45] Date of Patent: Nov. 14, 2000

[54] BALLOON OCCLUSION DIAMETER AND PRESSURE MEASURING DEVICES AND METHODS OF USE

[75] Inventor: Bruce Addis, Redwood City, Calif.

[73] Assignee: Embol-X, Inc., Mountain View, Calif.

[21] Appl. No.: 09/307,092

[22] Filed: May 7, 1999

[51] Int. Cl.[7] .................................................. A61M 29/00
[52] U.S. Cl. .................................... 604/100.03; 604/97.03
[58] Field of Search .............................. 604/96.01, 97.01, 604/97.02, 97.03, 98.01, 99.01, 100.01–100.03, 101.01; 606/192, 194

*Primary Examiner*—Wynn Wood Coggins
*Assistant Examiner*—Deborah Blyveis
*Attorney, Agent, or Firm*—Lyon & Lyon LLP

[57] ABSTRACT

The invention provides a device having first and second balloons. Each of the first and second balloons communicates with an inflation lumen. A differential pressure gauge communicates with both inflation lumens. Each of the inflation lumens also communicates independently with a pump for inflating the balloon. The pressure gauge may include a shut-off valve for terminating inflation in the second balloon when the pressure within the first balloon exceeds the pressure in the second balloon. The pressure gauge may also include a pressure limiter. Methods of using the devices for measuring diameter and pressure of a balloon occluder deployed in a vessel or body cavity are disclosed.

18 Claims, 2 Drawing Sheets

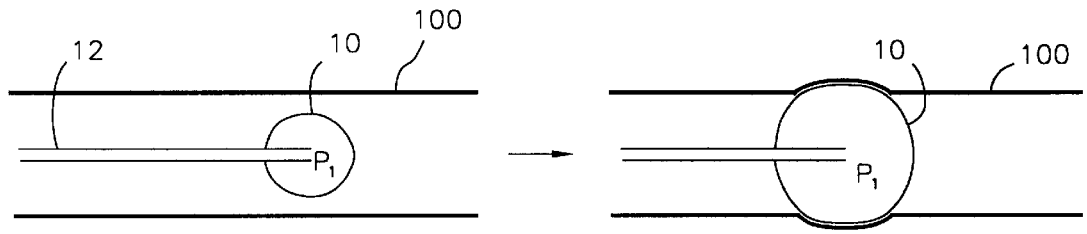
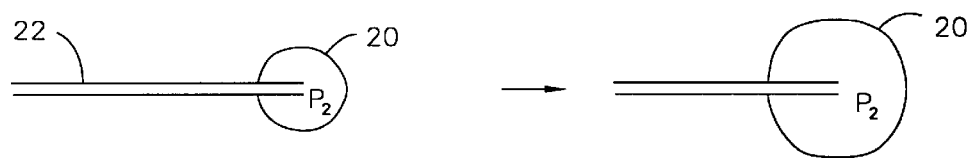
FIG. 2A           FIG. 2B
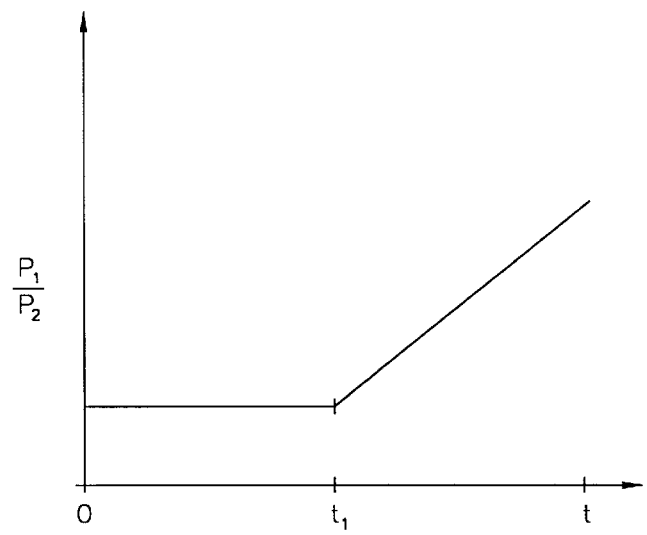
FIG. 2

BALLOON OCCLUSION DIAMETER AND PRESSURE MEASURING DEVICES AND METHODS OF USE

FIELD OF THE INVENTION

The present invention relates generally to medical devices useful for measuring the diameter and pressure of a balloon occluder deployed within a vessel. More particularly, the devices provide information on when the balloon occluder engages the vessel wall, diameter of the vessel wall, and force exerted on the vessel wall.

BACKGROUND OF THE INVENTION

Balloon occlusion devices are commonly deployed within a vessel during various cardiovascular surgeries to provide isolation of blood flow. During conventional or minimally invasive surgeries, including coronary artery bypass grafting, heart valve repair or replacement, septal defect repair, pulmonary thrombectomy, atherectomy, aneurysm repair, aortic dissection repair and correction of congenital defects, for example, circulatory isolation of the coronary blood flow from the peripheral vascular system is often required to establish cardiopulmonary bypass. Instead of using the traditional methods of aortic clamping, a balloon occluder is sometimes used to isolate blood flow in the aorta. Presently, balloon occluders are built to expand to the approximate lumenal diameter of the vessel, i.e., a balloon occluder with a smaller diameter would be used for the carotid artery while larger balloons are used in the aorta. Balloon occlusion devices are also used in other nonvascular procedures, such as dilation of an esophageal stricture in patients with achalasia, or dilation of an intra and/or extra-hepatic bile duct in patients with biliary stenosis.

There are several disadvantages associated with the current methods of inflating a balloon occluder in a vessel or body cavity. First, the optimal size of the balloon occluder for occluding the lumen of the vessel or the body cavity is unknown and is usually estimated according to the average lumenal diameter. The vessel may be affected by atherosclerosis, and the actual lumenal diameter may be reduced. Second, as the balloon is inflated to occlude the lumen of the vessel or body cavity, the point of contact of the perimeter of the balloon with the wall of the vessel or body cavity is uncertain. The operator can only estimate an acceptable level of wall distention. Third, the pressure generated by the expanded balloon on the wall of the vessel or body cavity is unknown. Complications due to over-inflation of the balloon may occur, including (1) atherosclerotic plaque rupture leading to distal embolization, (2) dissection of the vessel wall, (3) pseudoaneurysm formation due to subintimal hemorrhage, (4) aneurysm formation due to hyperextension and weakening of the vessel wall, (5) diverticulum formation due to weakening of the body tissue, and (6) vessel wall rupture or organ perforation.

New devices and methods are thus needed for balloon occlusion of a vessel or body cavity, in order to provide information on the effective diameter of the vessel or body cavity and allow an operator to optimally control the inflation of the balloon without damage to the vessel wall or body tissue.

SUMMARY OF THE INVENTION

The invention provides devices and methods for controlling the inflation of balloon occlusion devices. One embodiment of the devices includes first and second balloons. The first balloon is adapted for insertion into a patient's vessel or body cavity. The balloons may be elastomeric or non-elastomeric balloons. Each of the two balloons communicates with an inflation lumen. Each inflation lumen communicates independently with a pump for inflating the balloon. Both lumens communicate with a differential pressure gauge, which measures the pressure inside each balloon, compares both pressures, and displays the information.

In another embodiment, the pumps are syringes, which are adapted for infusion of air or fluid into the balloon. The syringes may operate in tandem for inflating the balloons simultaneously. In still another embodiment, the pressure gauge includes a shut-off valve, operably associated with the second inflation lumen. The valve enables the pressure gauge to terminate inflation into the second lumen and balloon after the pressure in the first balloon exceeds a certain threshold. In certain embodiments, the gauge may include a pressure limiter which limits the pressure in the first balloon from exceeding a set threshold, thereby avoiding over-inflation of the first balloon inside the vessel or body cavity.

The invention provides methods for measuring the pressure of a balloon occluder deployed in a patient's vessel or body cavity, e.g., bile duct. In a first method, using the devices described above, the first balloon is inserted through an incision into the lumen of a patient's vessel, e.g., aorta, or body cavity while maintaining the second balloon outside the patient's body. The first and second balloons are inflated simultaneously at the same rate of inflation by operating the pumps, which infuse air or fluid into the inflation lumens. The pressure within the first and second balloons are measured and compared by the differential pressure gauge, which comparison indicates when the first balloon engages the lumenal wall of the vessel or body cavity. As the first balloon contacts the vessel wall, the pressure in the first balloon rises disproportionately compared to the second balloon. The operator may then terminate inflation in the first balloon to avoid over-inflation.

In another method, when the pressure in the first balloon exceeds the pressure in the second balloon, the pressure gauge may activate the shut-off valve, thereby terminating the inflation of the second balloon. The gauge may be reset to measure the pressure within the first balloon and the atmosphere. In this way, any increase in the pressure in the first balloon is caused by the resistance of the vessel wall against the expanding balloon. The less compliant the vessel, e.g., artery with atherosclerotic plaque, the higher the resistance of the vessel wall and the higher the pressure registered in the pressure gauge. In the embodiment where the pressure gauge includes a pressure limiter, the limiter may sound an alarm when the pressure in the first balloon exceeds a set threshold, thereby avoiding complications associated with over-inflation of the balloon occluder.

It will be understood that there are several advantages to using the balloon occlusion measuring devices and methods disclosed herein. For example, the devices (1) notify the physician when the balloon contacts a vessel wall, (2) provide information on the diameter of the vessel wall, (3) provide information on pressure exerted on the vessel wall, (4) can be employed in any vessel with or without stenosis, (5) can be employed to occlude or dilate a body cavity, and (6) minimize complications associated with overinflation of the balloon occluder, i.e., wall rupture, dissection, pseudoaneurysm, and/or embolization.

BRIEF DESCRIPTION OF THE DRAWINGS

FIG. 2A depicts a first balloon deployed in the aorta and a second balloon outside the aorta.

FIG. 2B depicts the first balloon of FIG. 2A engaging the aortic wall.

FIG. 2 depicts a graph of the pressure differential between the first and second balloons versus time.

DETAILED DESCRIPTION

Figure 1:
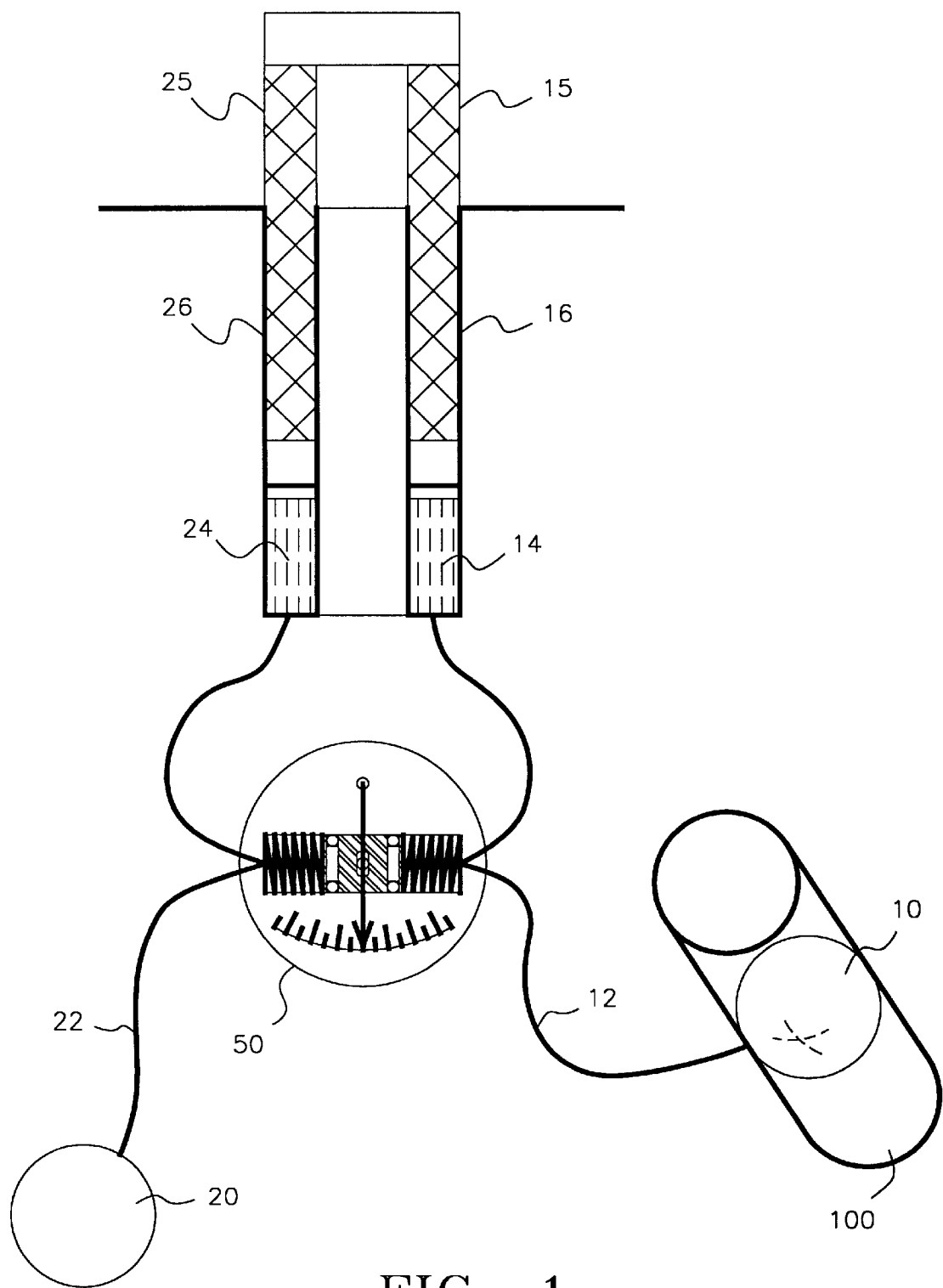
FIG. 1 depicts an embodiment of the balloon occluder pressure measuring device according to the present invention.

The balloon occluder pressure measuring devices and methods are most useful in providing optimal inflation of a balloon occluder deployed in a patient's vessel, e.g., aortic occlusion for cardiopulmonary bypass, and in preventing complications associated with balloon over-inflation. It will be understood that the devices and methods may also be used to provide optimal balloon inflation in occluding or dilating a patient's body cavity, e.g., the esophagus in patients with achalasia or the bile duct in biliary stenosis.

In FIG. 1, first balloon 10, which is inserted in the lumen of vessel 100, communicates with inflation lumen 12. Second balloon 20, which is outside the vessel, communicates with inflation lumen 22. Both lumens 12 and 22 communicate with differential pressure gauge 50. Inflation lumens 12 and 22 also communicate, respectively, with pumps 15 and 25, shown here as syringes. Syringe 16 has plunger 15 disposed within lumen 14 of the syringe. Syringe 26 has plunger 25 disposed within lumen 24 of the syringe. The syringes deliver air or fluid to the balloons through their respective inflation lumens. Proximal ends of plungers 15 and 25 may be activated in tandem to simultaneously inflate balloons 10 and 20. In use, after balloon occluder 10 is deployed in vessel 100, balloons 10 and 20 are inflated simultaneously, and at the same rate by advancing plungers 15 and 25 distally, forcing fluid or air through lumens 14 and 24 to inflate balloons 10 and 20. The pressure differential between balloons 10 and 20 is measured and indicated on pressure gauge 50.

In FIG. 2A, balloon 10, having pressure P1 inside the balloon, is deployed within vessel 100, and balloon 20, having pressure P2 inside the balloon, is outside the vessel. As both balloons are inflated, balloon 10 engages the wall of vessel 100 as shown in FIG. 2B. Once contact is achieved with the vessel wall, the pressure within balloon 10 rises disproportionatly to that of balloon 20, i.e., P1>>P2. The relationship between the pressure differential for balloons 10 and 20 (P1/P2) with inflation time (t) is illustrated in FIG. 2C. Time t1 indicates when balloon 10 engages the vessel wall as depicted in FIG. 2B. Before t1, the pressure differential between balloons 10 and 20 remains relatively constant. After t1, the pressure differential increases due to resistance from the vessel wall.

In the embodiments where the pressure gauge includes a shut-off valve operably associated with the second inflation lumen, inflation of balloon 20 may be terminated when the first balloon makes contact with the vessel wall. The gauge may be reset to measure the pressure within balloon 10 and the atmosphere, so that P1/P2 reflects the resistance generated by the vessel wall. The less compliant the vessel, e.g., artery with atherosclerosis plaque, the higher the resistance of the vessel wall. In this way, the devices provide the physician information on (1) when the balloon occluder device contacts the vessel wall, (2) the effective lumenal diameter of the vessel, and (3) force exerted on the vessel wall.

In still another embodiment, the pressure measuring device need not include a second balloon for pressure monitoring outside the body. In this embodiment, the physician carefully monitors the pressure gauge, noting when a significant pressure increase occurs (t=t1, when the balloon engages the vessel wall). Balloon inflation is then terminated to avoid vessel hyperextension.

The length of the inflation lumen will generally be between 10 and 200 centimeters, preferably approximately between 30 and 150 centimeters. The inner diameter of the inflation lumen will generally be between 0.05 and 0.5 centimeters, preferably approximately between 0.1 and 0.3 centimeters. The diameter of the expanded occluder will generally be between 0.3 and 2 centimeters, preferably approximately 0.5 and 1.0 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A balloon occlusion inflation apparatus, comprising:
   a first balloon enclosing a chamber which communicates with a first inflation lumen;
   a second balloon enclosing a chamber which communicates with a second inflation lumen;
   a differential pressure gauge communicating with the first inflation lumen and the second inflation lumen;
   a first pump communicating with the first inflation lumen; and
   a second pump communicating with the second inflation lumen.

2. The apparatus of claim 1, wherein the first and second balloons are elastomeric.

3. The apparatus of claim 1, wherein the first and second balloons are non elastomeric.

4. The apparatus of claim 1, wherein the first and second pumps are syringes.

5. The apparatus of claim 4, wherein the syringes are tandem acting syringes.

6. The apparatus of claim 1, wherein the pressure gauge includes a shut-off valve, operably associated with the second inflation lumen.

7. The apparatus of claim 1, wherein the pressure gauge includes a pressure limiter.

8. A method for occlusion of a vessel or body cavity, comprising the steps of:
   providing a balloon occlusion inflation apparatus comprising first and second balloons communicating respectively with first and second inflation lumens, each inflation lumen communicating with a differential pressure gauge;
   inserting the first balloon into the lumen of a vessel or body cavity while maintaining the second balloon outside of the vessel; and
   inflating the first and second balloons simultaneously and at the same rate of inflation, wherein the differential pressure gauge indicates when the first balloon engages the lumenal wall of the vessel or body cavity.

9. The method of claim 8, further comprising a first pump communicating with the first inflation lumen and a second pump communicating with the second inflation lumen.

10. The method of claim 9, wherein the first and second pumps are syringes.

11. The method of claim 10, wherein the syringes are tandem acting syringes.

12. The method of claim 8, wherein the first and second balloons are elastomeric.

13. The method of claim 8, wherein the first and second balloons are non-elastomeric.

14. The method of claim 8, further comprising the step of terminating the inflation in the second balloon when the pressure in the first balloon exceeds the pressure in the second balloon.

15. The method of claim 8, wherein the vessel is an artery.

16. The method of claim 15, wherein the artery is the aorta.

17. The method of claim 8, wherein the body cavity is the esophagus.

18. The method of claim 8, wherein the body cavity is the bile duct.

\* \* \* \* \*